United States Patent [19]
Afromowitz et al.

[11] 4,133,735
[45] Jan. 9, 1979

[54] ION-SENSITIVE ELECTRODE AND PROCESSES FOR MAKING THE SAME

[75] Inventors: Martin A. Afromowitz; Sinclair S. Yee, both of Seattle, Wash.

[73] Assignee: The Board of Regents of the University of Washington, Seattle, Wash.

[21] Appl. No.: 837,279

[22] Filed: Sep. 27, 1977

[51] Int. Cl.$^2$ .................... G01N 27/30; G01N 27/36; B05D 1/18; C23B 15/00

[52] U.S. Cl. .......................... 204/195 G; 29/592 R; 128/2 E; 204/192 SP; 204/195 M; 427/123; 427/124; 427/125

[58] Field of Search ........ 204/195 M, 195 G, 192 SP; 128/2 E, 2.1 E; 29/592 R; 324/29, 30 R; 427/123, 124, 125

[56] References Cited

U.S. PATENT DOCUMENTS

| 3,929,609 | 12/1975 | Gray et al. | 204/1 T |
| 4,031,606 | 6/1977 | Szonntagh | 29/570 |

OTHER PUBLICATIONS

P. N. Setty, "Fabrication of a Solid State Electrode to Determine the Calcium Ion Conc. in Blood", 5/1976.
M. Semler et al., J. Electroanal. Chem. & Interfacial Electrochem., vol. 56, No. 1, pp. 155-159, Oct. 1974.
F. A. Lowenheim, "Modern Electroplating", p. 606 (1963).

*Primary Examiner*—G. L. Kaplan
*Attorney, Agent, or Firm*—Christensen, O'Connor, Johnson & Kindness

[57] ABSTRACT

An improved ion-sensitive electrode is described, particularly in terms of the structure of a pH electrode and first and second processes for making the same. The pH electrode includes a substrate, preferably of forsterite, which is configured as a wafer having a substantially planar wafer surface. A continuous conducting layer, formed by either thin-film vapor deposition or thick-film screening processes, is formed on the substantially planar wafer surface in a desired configuration. A first region of the continuous conducting layer, and contiguous portions of the substantially planar wafer surface, are covered by a continuous membrane layer preferably composed of a pH-sensitive glass such as Corning Code 0150 glass. Typically, the membrane layer is formed by a thick-film process which involves the reduction of the glass to a fine powder, the mixing of the powder with an organic vehicle including an organic solvent and an organic binder to form a glass paste, and the application of the glass paste to the wafer through a wire mesh screen having an open region therethrough corresponding in configuration to that of the desired membrane layer. The paste when applied to the wafer is fused into a continuous membrane layer by the application of heat, at a first temperature to drive off the organic solvent and at a second temperature or temperatures to drive off the organic binder and to fuse the glass. An insulated output lead is connected directly to a second region of the conducting layer. Alternatively, an active device chip, such as that including a field effect transistor, is bonded to the wafer and interconnected with the second region of the conducting layer and with the output lead or leads. The exposed conducting elements of the electrode, including the second region of the conducting layer, the active device chip, and all exposed portions of the leads, are covered by a fluid-tight seal. Other ion-sensitive electrodes and variations of the aforementioned processes are described.

96 Claims, 10 Drawing Figures

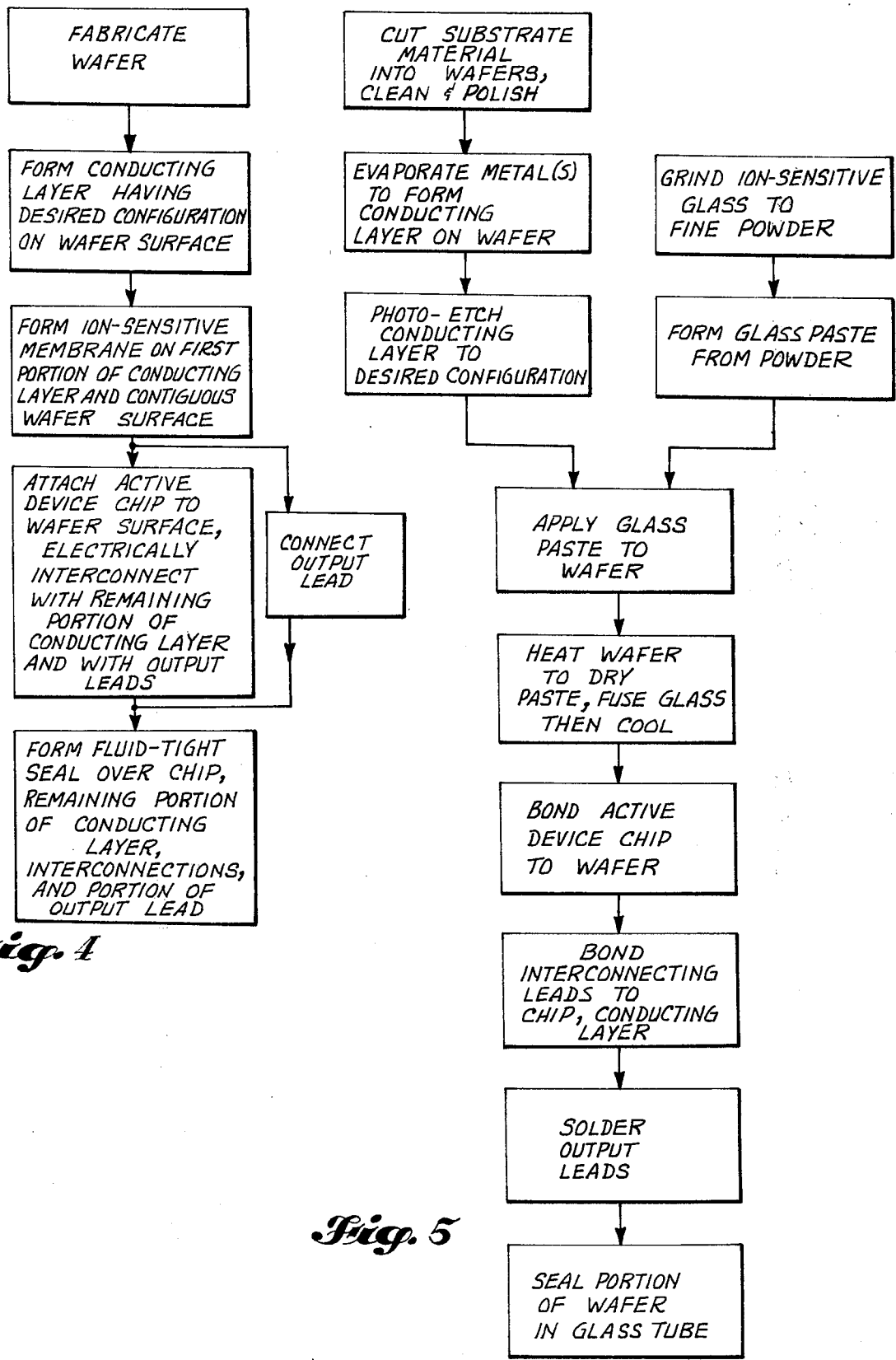

ION-SENSITIVE ELECTRODE AND PROCESSES FOR MAKING THE SAME

The invention described herein was made in the course of work under a grant or award from the Department of Health, Education and Welfare.

FIELD OF THE INVENTION

This invention generally relates to ion-sensitive electrodes and processes for making the same, and more particularly, to such ion-sensitive electrodes which include an ion-exchanging membrane for developing a potential related to the activity of a specific ion in a solution.

BACKGROUND OF THE INVENTION

Ion-sensitive electrodes are known to the prior art for use in measuring the activity of a specific ion, or ions, in a test solution. In the case where the test solution comprises bodily fluids, the ion activities typically measured are those of the hydrogen, sodium, potassium, and calcium cations (respectively $H^+$, $Na^{30}$, $K^+$, and $Ca^{2+}$). Typically, the ion-sensitive electrode are a reference electrode are immersed in the test solution. The ion-sensitive electrode may, in one instance, be constructed with an ion-exchanging membrane so that the potential difference between the ion-exchanging membrane and the test solution is a function of the activity of a particular ion in the test solution. The reference electrode is constructed so that the potential difference between the reference electrode and the test solution is a constant independent of the composition of the test solution. By measuring the voltage across the ion-sensitive electrode and the reference electrode, the activity, and therefore the concentration, of a particular ion in the test solution may be determined.

The construction of a typical ion-sensitive electrode known to the prior art for measuring the activity of hydrogen ions (otherwise referred to as a pH electrode) is seen in FIG. 1. A metallic conductor 10, typically a silver wire coated with silver chloride, is immersed in an inner reference solution 12, typically composed of a weak hydrogen chloride or other solution having a known and constant pH, which is contained within a sealed glass tube 14. One end of the tube 14 is closed by a thin membrane 16 which is handblown from a pH-sensitive glass. It is known in the prior art that when certain glasses, for example, that marketed by Corning Glassworks as Code 0150 glass, having a norminal mole-percent composition of 22%, $Na_2O$, 6% CaO, and 72% $SiO_2$, are constructed in very thin membranes (less than 100 microns) and immersed in a test solution, a very thin hydrated layer (typically 100 Å) is formed on the membrane surface in contact with the test solution which apparently permits the exchanger of sodium ions in the glass for hydrogen ions in the test solution. The result of this ion exchange is the development of a potential difference between the membrane and the test solution which is related to the hydrogen ion activity in the test solution.

The overall potential difference between the metallic conductor 10 and the test solution may be visualized as the sum of the potential differences between the metallic conductor 10 and the inner reference solution 12; across the inner reference solution 12; between the inner reference solution 12 and the membrane 16; across the membrane 16; and, between the membrane 16 and the test solution. It has been shown that all of these potential differences, with the exception of the potential difference between the membrane 16 and the test solution, are substantially constant with respect to the pH of the test solution.

Since the potential difference between the reference electrode and the test solution is substantially constant and independent of pH, the potential difference between the pH electrode and the reference electrode, when immersed in the test solution, varies linearly with pH at a given temperature according to the well-known equation $$V_{pH} = V_o - \frac{kT(\ln 10)}{e} \cdot (pH)$$

where $V_o$ is an electrode-dependent contant, k is Boltzmann's constant, T is the temperature of the test solution in degrees Kelvin, e is the charge on an electron, and pH is the hydrogen ion concentration of the test solution in pH units. At room temperature of 300° Kelvin, the potential difference changes linearly by approximately 59mv/pH unit.

While pH electrodes of the aforementioned construction provide acceptable pH response in industrial or medical applications in which the pH electrode is immersed in a test solution contained within a receptacle, they have proved unsuitable for in vivo medical applications in which the pH electrode and the reference electrode are brought into contact with bodily fluids contained within a body receptacle or cell. Experimenters in the prior art have sought to construct ion-sensitive electrodes, including pH electrodes, for in vivo applications by reducing the dimensions of the ion-sensitive electrodes to dimensions compatible with body receptable and cellular structure. Such electrodes, oftentimes termed "microelectrodes" are difficult to make, inasmuch as a highly trained glass blower must blow the glass membrane of the electrode by hand. Because of their small size, such microelectrodes are very fragile and thus structurally unsuitable for most in vivo applications. The fragility of the microelectrodes also requires that a large quantity of such microelectrodes be fabricated in order to achieve a required number of acceptable microelectrodes due to microelectrode breakage. Since each microelectrode is handmade, uniformity cannot be guaranteed among microelectrodes so that detailed calibration tests must be run. Because of the aforementioned difficulty of manufacture, fragility, and testing procedures, individual microelectrodes are quite expensive and are therefore uneconomic for in vivo applications in which a large number of such microelectrodes may be used and then disposed of.

In attempts to construct acceptable microelectrodes for in vivo medical applications, experimenters have developed various types of solid-state devices fabricated by means of certain thin-film integrated circuit techniques. Among these solid-state devices are those identified as CHEMFETs or ISFETs, standing, respectively, for chemically-sensitive and ion-sensitive field effect transistors. In these devices, the conductor normally applied to a gate insulating region of the field effect transistor is not utilized, and the gate insulating region is itself fabricated out of an ion-sensitive material. Because the ion-sensitive material must be bonded to the substrate of the field effect transistor, typically high purity silicon, and must be limited in its thickness to typically less than a micron, the only ion-sensitive materials conveniently fabricated in the prior art by thin-film techniques on a silicon substrate are silicon dioxide ($SiO_2$) or silicon nitride ($Si_3N_4$), or a combination of these materials. Accordingly, the best-characterized and desirable membrane materials, including ion-sensitive glasses such as Corning Code 0150 glass, cannot be used.

The experimenters of the prior art have also attempted to dispense with the inner reference solution by providing an ion-sensitive electrode in which a metallic conductor is in direct contact with an ion-sensitive, glass membrane. These electrodes, often referred to as "metal-connected" glass electrodes, typically are constructed by plating or otherwise applying a metallic conducting layer directly on a performed member including a thin membrane of the desired ion-sensitive glass. As yet another example of such metal-connected glass electrodes, an element comprising a conductor has a surface layer of an electrochemically active metal. This surface layer is coated with a first coating of a mixture of glass and a halide of the active metal. Preferably, the active metal is copper and the halide is copper chloride. An ion-sensitive glass membrane, or second coating, is then formed over the first coating by dipping the conductor into a molten bath of ion-sensitive glass so as to cover entirely the first coating. The conductor is then removed from the molten bath and the glass is allowed to cool and to solidify into the desired membrane.

While such metal-connected glass electrodes of course dispense with the need for an inner reference solution and are more rugged in their construction than ion-sensitive electrodes including such an inner reference solution, they have not been capable of providing repeatable and determinable responses to specific ion activities.

There are quite a number of other ion-sensitive electrodes, and processes for making the same, that have been proposed in the prior art and that are subject to one or more of the shortcomings of the prior art ion-sensitive electrodes discussed in detail herein.

It is therefore an object of this invention to provide an improved ion-sensitive electrode.

It is a further object of this invention to provide such an improved ion-sensitive electrode which can be fabricated as a microelectrode suitable for in vivo medical applications.

It is yet a further object of this invention to provide such an improved ion-sensitive electrode fabricated as a microelectrode which is rugged in construction, and which can be inexpensively mass-produced.

It is another object of this invention to provide microelectrodes which, when mass-produced, exhibit repeatable and determinable responses to specific ion activities.

It is still another object of this invention to provide an improved ion-sensitive electrode which is electrically stable, low in noise and electronically compatible with standard silicon-based integrated circuits.

Yet another object of this invention is to provide an ion-sensitive electrode which can be fabricated by thin-film and thick-film integrated circuit processes, and various combinations thereof.

Still another object of this invention is to provide thin-film and thick-film integrated circuit processes for fabricating ion-sensitive electrodes.

A further object of this invention is to provide thin-film and thick-film integrated circuit processes for ion-sensitive electrodes which permit the best-characterized and desirable membrane materials, including ion-sensitive glasses, to be used.

Still a further object of this invention is to provide thin-film and thick-film integrated circuit processes which permit ion-sensitive electrodes to be inexpensively and uniformly mass-produced.

It is also an object of this invention to provide an improved ion-sensitive electrode, and processes of making the same, which eliminates in most cases the need for the inner reference materials used in prior art ion-sensitive electrodes.

A particular object of this invention is to provide an improved pH electrode, suitable for in vivo medical applications, and processes for making such an improved pH electrode.

SUMMARY OF THE INVENTION

Briefly, these objects and others that will be apparent to those of ordinary skill in the art are achieved in the following manner.

An improved ion-sensitive electrode constructed according to the teachings of the present invention comprises a substrate having a substrate surface. A conductor is bonded to the substrate, the conductor having first and second regions, with at least the first region being formed as a conducting layer on the substrate surface. An ion-sensitive membrane is bonded to the substrate and to a portion of the conductor, the membrane including at least a continuous membrane layer covering the first region of the conductor and portions of the substrate surface which are contiguous to the first region. An output means is electrically interconnected with the second region of the conductor for connecting the electrode to a utilization device. Finally, a fluid-tight sealing means is bonded to the substrate and to the conductor and covers at least the second region of the conductor and portions of the substrate surface and output means adjacent the second region of the conductor.

An ion-sensitive electrode of the type described may be fabricated by fabricating a wafer from a substate material, the wafer having a substantially planar surface; forming a continuous conducting layer having a desired configuration on the substantially planar wafer surface; forming a continuous ion-sensitive membrane layer on a first region of the continuous conducting layer and contiguous portions of the substantially planar wafer surface; connecting at least one lead to a second region of the continuous conducting layer; and, forming a fluid-tight seal, over the second region of the continuous conducting layer, contiguous portions of the substantially planar wafer surface and a portion of the lead adjacent the second region of the continuous conducting layer.

The conducting layer itself may be formed by either a thin-film vapor deposition process, or by a thick-film screening process. In the former case, the substantially planar wafer surface is polished and cleaned. The wafer is then placed into an evacuated chamber along with a quantity of at least one metal and the metal is heated to a temperature sufficient to vaporize the metal so that the metal uniformly deposits throughout the chamber and in a continuous conducting layer on at least the substantially planar wafer surface. The wafer is removed from the evacuated chamber. The continuous conducting layer is then photoetched to the desired configuration. In the latter case, a first wire mesh screen is prepared, the first wire mesh screen having a predetermined mesh and a thickness approximating that of the desired conducting layer. The first wire mesh screen also has an open region therethrough corresponding in configuration to that of the desired conducting layer. A paste is prepared by mixing, with an organic vehicle including an organic solvent and an organic binder, a conducting material in particle form, and having an average particle size less than the predetermined mesh of the first wire mesh screen. The first wire mesh screen is brought into contact with the substantially planar wafer surface and the paste is spread on the wire mesh screen so as to cover at least the open region therethrough. The paste is then forced through the open region in the first wire mesh screen and into contact with the substantially planar wafer surface. The wire mesh screen is removed, whereupon the paste adheres to the wafer surface with the configuration of the desired conducting layer, and the wafer is heated to a first temperature for a time sufficient to drive off the organic solvent and then to at least a second temperature for a time sufficient to drive off the organic binder and to fuse the conducting material of the paste into a continuous conducting layer, and allowed to cool.

The continuous ion-sensitive membrane layer is preferably formed by a thick-film screening process. In this process, ion-sensitive material, such as ion-sensitive glass, is reduced to a fine powder and mixed with an appropriate organic vehicle including an organic solvent and an organic binder to form a glass paste. A second wire mesh screen is prepared which has a predetermined mesh and a thickness approximating that of the desired membrane layer. The second wire mesh screen also has an open region therethrough corresponding in configuration to that of the desired membrane layer. The seond wire mesh screen is then brought into contact with the substantially planar wafer surface so that the open region therethrough is in registration with the continuous conducting layer, and the glass paste is applied to the second wire mesh screen so as to cover at least the open region therethrough. The glass paste is then forced through the open region in the second wire mesh screen and into contact with the first region of the continuous conducting layer and contiguous portions of the substantially planar wafer surface. The second wire mesh screen is removed, whereupon the glass paste adheres to the wafer in the configuration of the desired membrane layer, and the wafer is heated to a first temperature for a period of time sufficient to drive off the organic solvent and then to at least a second temperature for a period of time sufficient to drive off the organic binder and to fuse the glass into a continuous membrane layer. Thereafter, the wafer is quickly quenched to substantially room temperature.

The structure and processes of the present invention permit an active device chip, such as that including a field effect transistor, to be bonded to the wafer, preferably to the substantially planar wafer surface, and to be interconnected with the second region of the continuous conducting layer and an output lead or leads for connection of the electrode to a utilization device. In this case, the fluid-tight seal is formed additionally over the active device chip and all exposed interconnections. If desired, the conducting layer may also be configured in the form of one or more pads which are isolated from the second region of the conducting layer on the substantially planar wafer surface, and the active device chip may be bonded to the substantially planar wafer surface and interconnected with the second region of the conducting layer and one or more of the pads by appropriate interconnecting leads, with an output lead or leads being bonded, such as by soldering, to one or more of the conducting pads.

BRIEF DESCRIPTION OF THE DRAWINGS

The invention can be best understood by reference to the following portion of the specification taken in conjunction with the accompanying drawings, in which:

FIG. 4 is a flow chart illustrating the basic process steps in the fabrication of improved ion-sensitive electrodes according to the teachings of the present invention;

FIG. 5 is a flow chart illustrating the specific process steps of a first process of the present invention and utilizing in part thin-film integrated circuit techniques;

DESCRIPTION OF THE PREFERRED EMBODIMENT

In order that those skilled in the art may fully comprehend the present invention, the description that follows will in large part concern the structure and fabrication of pH electrodes by two separate processes. As will be discussed hereinafter, the present invention is not limited to such pH electrodes, but rather is applicable in general to ion-sensitive electrodes and processes of making the same.

ION-SENSITIVE ELECTRODE

Figure 1:
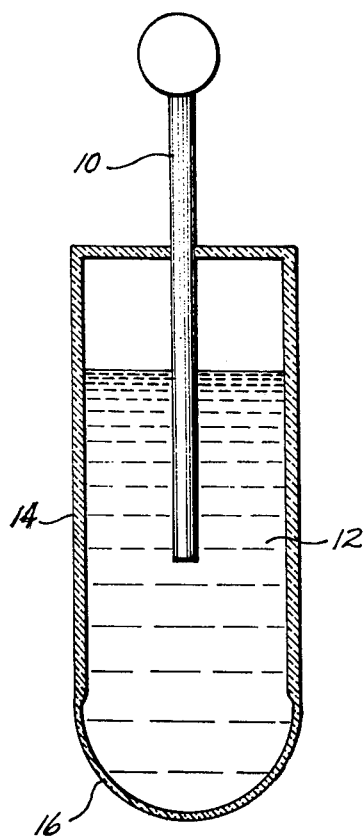
FIG. 1 is a schematic representation of the pH electrode as known to the prior art and as previously discussed.
Figure 2:
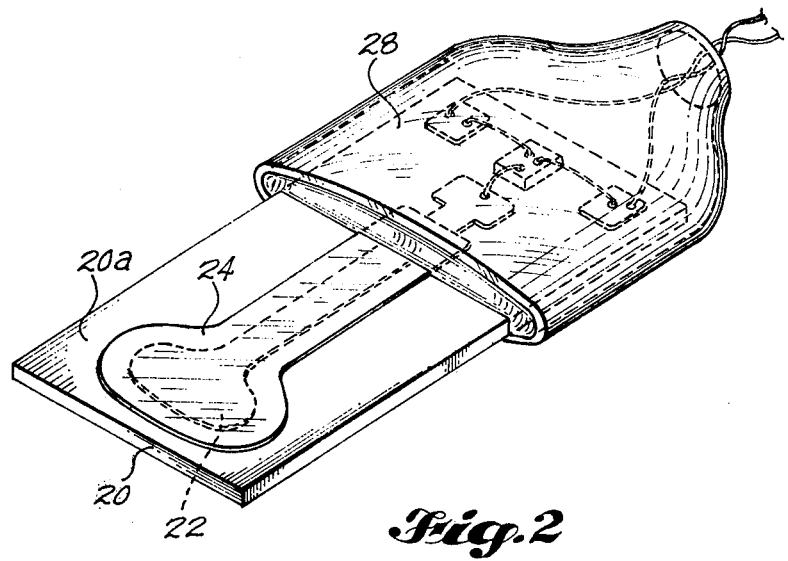
FIG. 2 is a pictorial view of the preferred embodiment of the improved ion-sensitive electrode of the present invention.
Figure 3:
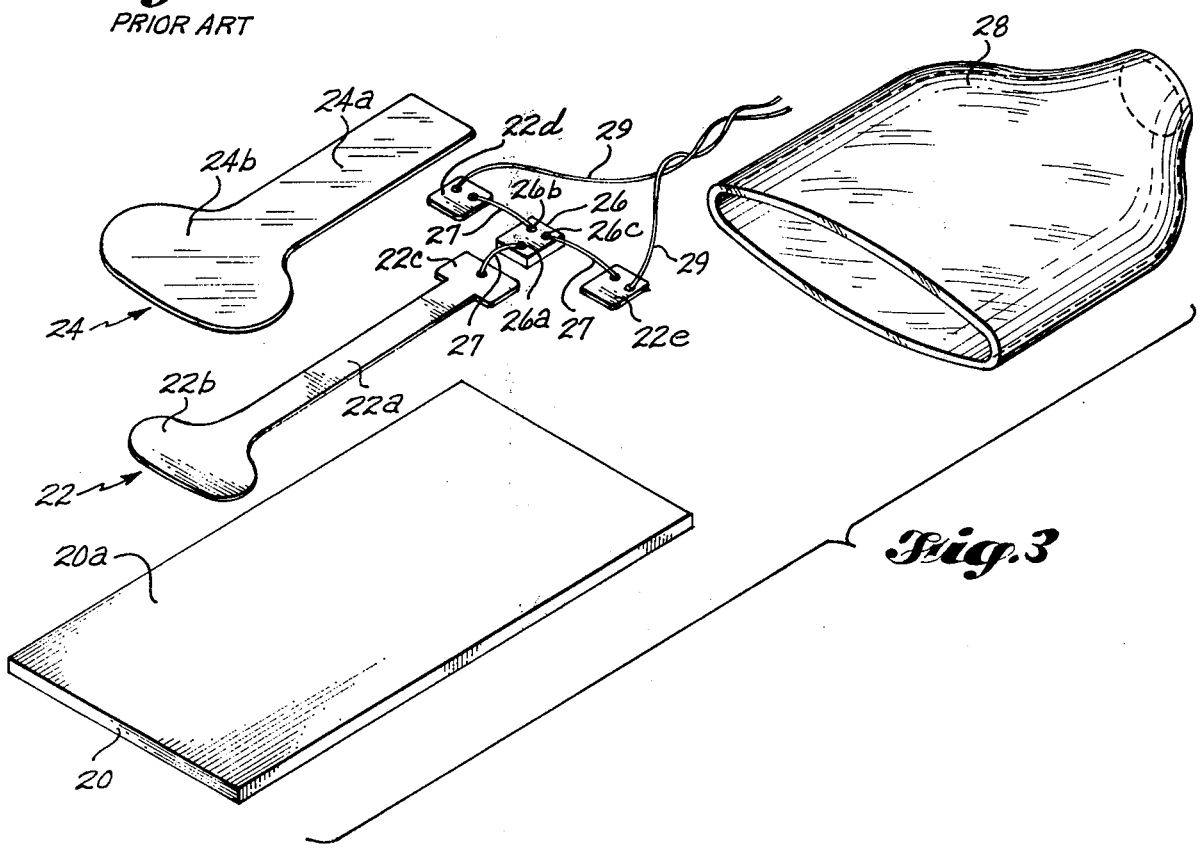
FIG. 3 is an exploded pictorial view corresponding to FIG. 2.

Referring now to FIGS. 2 and 3, the ion-sensitive electrode illustrated therein includes a substrate 20, a conductor including a conducting layer 22, an ion-sensitive membrane layer 24, and active device chip 26, and a seal 28.

The substrate 20 is in the form of a substantially rectangular, flat wafer and is preferably composed of a ceramic material. The conducting layer 22 is preferably applied to a substantially planar surface 20a of the substrate 20 and has the configuration of an elongated strip 22a having opposite, enlarged ends 22b, 22c, and first and second pads 22d, 22e which are electrically and physically isolated from each other and from the conducting strip 22a adjacent end 22c thereof. The ion-sensitive membrane layer 24 overlies a first portion of the conductor and has, in this example, the configuration of an elongated strip 24a overlying the strip 22a and contiguous portions of the substantially planar surface of substrate 20, with strip 24a having an enlarged end 24b which overlies the enlarged end 22b of the strip 22a and contiguous portions of the surface of the substrate 20. It will be particularly noted that a second region of the conductor is not covered by the ion-sensitive membrane layer 24, the second region including in this example the enlarged end 22c and adjacent portions of the strip 22a. The active device chip 26, typically including a field effect transistor (FET), is bonded to the substrate 20 and, preferably to the substantially planar surface 20a thereof to which the conducting layer 22 and ion-sensitive membrane layer 24 are applied. Typically, the active device chip 26 includes an input terminal 26a and a pair of output terminals 26b, 26c which are respectively electrically interconnected with enlarged end 22c, and pads 22d, 22e by a plurality of interconnecting leads 27. In the case where the active device chip 26 comprises a field effect transistor, the terminals 26a, 26b and 26c represent, respectively, the gate, source and drain terminals thereof. A pair of insulated output leads 29 are also bonded to pads 22d, 22e to allow the ion-sensitive electrode to be electrically interconnected with an indicating meter, not illustrated, to which is also connected the reference electrode required for ion concentration measurements.

The seal 28 is seen to completely surround that portion of the substrate 20 on which are located the end 22c of the strip 22a, the isolated pads 22d, 22e, the active device chip 26, the interconnecting leads 27, and a portion of the insulated output leads 29. In addition, the seal 28 overlies a portion of the elongated strip 24a of the ion-sensitive membrane layer 24 and functions to block the bodily fluid or other test solution in which the electrode is immersed from contacting and therefore shorting the conducting elements of the electrode.

pH ELECTRODE

The choice of materials for the ion-sensitive electrode is in large part determined by the physical and chemical properties of the material utilized for the ion-sensitive membrane layer 24, and by the type of proces that is used to form both the conducting layer 22 and the ion-sensitive membrane layer 24 on the substrate 20. For pH electrodes, a well-known and desirable material is the aforementioned Corning Code 0150 glass. As explained in more detail hereinafter, the pH-sensitive glass forming the membrane layer 24 must be able to bond to the substrate 20 and the substrate 20 must have a thermal coefficient of expansion which matches that of the pH-sensitive glass due to the fact that the substrate 20 is heated and cooled in formation of the membrane layer 24. Using these considerations and others, a good choice of material for the substrate 20 in the case where the membrane layer 24 is formed from Corning Code 0150 glass is that ceramic material known as forsterite which comprises a hot-pressed mixture of magnesium oxide (MgO) and silicon dioxide ($SiO_2$).

The choice of materials for the conducting layer 22 is determined in part by the desirability of achieving a good bond between the conducting layer 22 and the underlying substrate 20, and between the conducting layer 22 and the overlying membrane layer 24. In addition, the conducting layer 22 must not be significantly adsorbed into the overlying membrane layer 24, must comprise a good electrical conductor, and must be capable of having the leads 27 and 29 easily soldered or bonded thereto. In the examples discussed hereinafter, the conducting layer 22 may, in a first instance, be formed by forming successive, thin-film layers of chromium, nickel, gold and silver on the substrate 20 in the desired configuration. In this structure, the chromium provides a good bond to the ceramic material of he substrate 20, the nickel improves solderability of the output leads 29, the gold provides a good, inert conductor which is not absorbed into the overlying membrane layer 24, and the silver provides a good bond between the conducting layer 22 and the overlying membrane layer 24. In a second instance, the conducting layer 22 may be formed by forming a thick-film layer of a platinum-gold mixture in the desired configuration on the substrate 20, in which instance the platinum-gold mixture provides good bonding between the conducting layer 22 and the underlying substrate 20 and overlying membrane layer 24, permits bonding and soldering of the leads 27 and 29, and provides a good, inert conductor not absorbed into the membrane layer 24.

The length and width dimensions of the conducting layer 22 and the membrane layer 24, as well as the exact configuration of those layers, is not critical, but must be chosen so as to maximize the surface area of the first region of the conducting layer 22 since the electrical impedance between the conducting layer 22 and the test solution varies inversely with the surface area of the first region of the conducting layer 22. The dimensions of the substrate 20 in turn are determined by the desired overall physical dimensions of the finished electrode. The thickness of the substrate 20 is determined by balancing the desire for physical ruggedness of the finished electrode with the desire for small size thereof. The thickness of the conducting layer 22 is not critical, but must not be so great such that it is difficult to cover the edge of the conducting layer 22 with the membrane layer 24. However, the thickness of the membrane layer 24 is limited to that which will provide acceptable pH response, which, in the case of Corning Code 0150 glass, is less than 100 microns.

As an example, pH electrodes made by the processes to be hereinafter described utilized substrates which were configured as wafers approximately 1.5 mm. wide $\times 5$ mm. long $\times 0.5$ mm. thick, with a conducting layer 22 having an average thickness of approximately 25 microns, and with a membrane layer 24 having an average thickness of no more than 50 microns.

pH sensitive glasses such as Corning Code 0150 glass have a very high electrical impedance. Since the magnitude of the pH-related, electrical output signal of pH electrodes using such pH sensitive glasses is quite low (on the order of millivolts), it has been required in the prior art to electrically interconnect the pH electrode with an indicating meter by means of a bulky, shielded, coaxial cable to prevent noise signals from masking the pH-related signal. To avoid the use of such a coaxial cable, the present invention includes the active device chip 26 which is formed as an integral part of the pH electrode and which functions to convert the high electrical impedance of the membrane layer 24 to a substantially lower electrode output impedance so that the pH electrode can be interconnected with an indicating meter by relatively thin, unshielded leads. Preferably, the active device chip 26 comprises a field effect transistor of the metal-oxide-semiconductor type, and typically formed by thin-film depositions upon a silicon substrate. The silicon substrate is compatible with the ceramic material of the substrate 20 so that the active device chip 26 can be bonded directly to the substrate 20. Further, the separation of the active device chip 26 from the membrane layer 24 ensures that both the active device chip 26 and the membrane layer 24 may be bonded to the same substrate 20.

Figure 10:
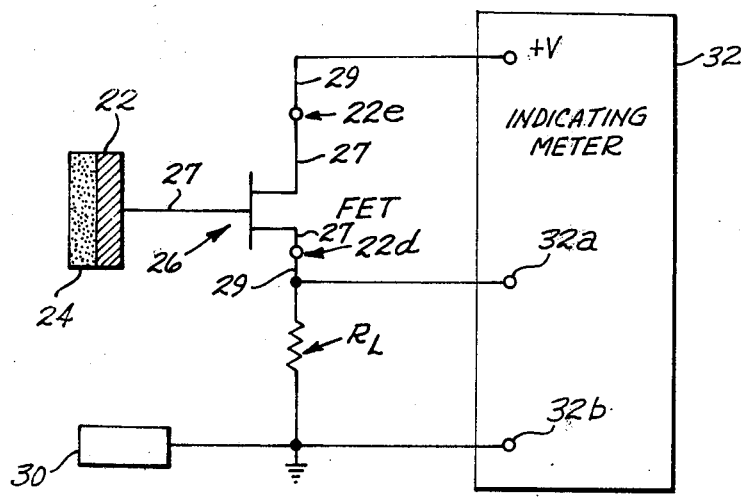
FIG. 10 is a schematic circuit diagram of the improved ion-sensitive electrode in circuit with a reference electrode.

Now referring to FIG. 10, the active device chip 26 is seen to comprise an FET whose gate terminal is connected by one of the leads 27 to the conducting strip 22. The drain terminal of the FET is connected by another one of the leads 27 to the pad 22e which in turn is connected by one of the output leads 29 to a source of positive potential +V located at a DC-coupled, direct-reading indicating meter 32. The source terminal of the FET is connected by yet another one of the leads 27 to the pad 22d which in turn is connected by the other output lead 29 to a first input terminal 32a of the indicating meter 32. A reference electrode 30 is connected to the other input terminal 32b of the indicating meter 32, and a load resistor $R_L$ is connected across the indicating meter input terminals 32a, 32b. Those skilled in the art will recognize the circuit in FIG. 10 as a typical source-follower circuit in which the high electrical impedance of the electrode, including that of the membrane layer 24, is converted into a relatively low impedance across the input terminals 32a, 32b of the indicating meter 32. As a result, the pH-related signal developed at the interface between the membrane layer 24 and the test solution is efficiently coupled to the indicating meter 32 so that relatively thin, unshielded leads, such as leads 29, can be used. Another advantage resulting from the use of the active device chip 26 is that the response time of the electrode is significantly reduced. This occurs because the capacitance of the FET gate is much smaller than that of the coaxial cable typically used to interconnect the prior art electrodes with an indicating meter. Hence, the time required to change potential by charging or discharging the FET gate capacitance is also smaller. Consequently, the response time of the electrode to changes in pH is significantly reduced.

When the pH electrode is immersed in the test solution, the conducting layer 22 must be kept out of contact with the test solution so that a short is not developed between the test solution and the conducting layer 22. The overlapping of the membrane layer 24 onto portions of the substrate 20 contiguous to the conducting strip 22 of course seals a portion of the conducting layer 22 from contact with the test solution. However, the portion of the conducting layer 22 that is not covered by the membrane layer 24, as well as the active device chip 26, and the leads 27 and 29, must also be maintained out of contact with the test solution, and for this purpose the seal 28 is provided. The seal 28 may be formed from a flattened, non-pH-sensitive glass tube which is filled with an epoxy resin which is allowed to cure. Alternatively, the seal 28 may be formed from heat-shrinkable tubing, such as that composed of polyvinyl chloride, which is filled with an appropriate hydrophobic potting material such as beeswax, with the heat-shrinkable tubing and beeswax being heated when the substrate 20 has been partially placed therein to form the seal 28.

PROCESS—GENERAL

With reference now to FIG. 4, the general process steps used in the fabrication of ion-sensitive electrodes, including pH electrodes, will be discussed.

In the first step, the desired substrate material is fabricated into wafers having the desired substrate thickness. Typically, the substrate material is obtained in block form and cut into wafers of the desired thickness by using a diamond-tipped disc saw. After cutting, the wafers are cleaned to remove contaminants and polished if necessary to obtain a smooth, substantially planar surface upon which the conducting and membrane layers may be formed.

The length and width of each wafer is determined by the number of ion-sensitive electrodes that are to be fabricated at one time, since the thin-film and thick-film processes to be described allow the fabrication of a plurality of ion-sensitive electrodes upon a single wafer.

In the next step of the process, a conducting layer having the desired configuration is formed on the wafers. In the first process to be described in detail hereinafter, each wafer is placed in an evacuated chamber along with a desired metal or metals and the metal is heated until it vaporizes and uniformly deposits on at least the substantially planar surface of the wafer. If more than one metal layer is to be placed upon the wafer surface, then the metals are vapor deposited in a desired sequence. A photographic mask is prepared which has an array of spaced-apart sets of apertures therein, each set of apertures being patterned in the configuration of the desired conducting layer for each finished electrode. The photographic mask is then brought into contact with a substantially planar surface of the wafer and a photoresist material previously applied to the wafer surface is exposed and developed. Thereafter, the wafer is dipped in an etching solution to remove all of the deposited metal excepting that which is covered by the developed photoresist material, and the developed photoresist material is removed with acetone to leave an array of conducting layers on the wafer surface.

In the second process to be described in detail hereinafter, a flat wire mesh screen is prepared which is covered with photoresist material except for an array of spaced-apart sets of regions thereof, each set of regions being patterned in the configuration of the desired conducting layer for each finished electrode. The wire mesh screen is then brought into contact with a substantially planar surface of the wafer and a paste including the desired materials of the conducting layer, in a fine particle form, is placed on top of the screen. A squeegee is drawn over the wire mesh screen to force the paste through the sets of regions in the screen and into contact with the wafer surface. When the wire mesh screen is removed, the wafer surface will have located thereon an array of paste layers. The wafer is then placed into a furnace and heated, first to a temperature sufficient to dry the paste, and second to a higher temperature sufficient to melt the materials within the paste into an array of continuous conducting layer patterns.

After cooling, the ion-sensitive membrane layer is formed on a portion of each conducting layer and contiguous portions of the wafer surface. In the first process to be described hereinafter, the ion-sensitive material, such as an ion-sensitive glass, is ground into a fine powder and mixed with an organic vehicle to form a glass paste. The glass paste is then applied by hand in a thin layer so that the paste covers the desired portion of each conducting layer and contiguous portions of the wafer surface. The wafer is then heated to a temperature to dry the glass paste and then to a higher temperature to fuse the glass into a continuous membrane layer, and allowed to cool.

In the second process to be described hereinafter, a flat wire mesh screen is prepared which is covered with photoresist material except for an array of spaced-apart regions thereof, each region being patterned in the configuration of the desired membrane layer for each finished electrode. The wire mesh screen is then brought into contact with the wafer surface so that the array of regions thereof are aligned with the array of conducting layers, and a glass paste formed as previously described is placed on the wire mesh screen. A squeegee is then used to force the glass paste through the array of regions. Upon removal of the screen, the wafer surface will have located thereon an array of glass paste layers. The wafer is then heated, first to a temperature to dry the glass paste and second to a higher temperature to fuse the glass into a continuous membrane layer, and then allowed to cool.

In the next step of the process, the wafer is cut into individual electrodes, again using a diamond-tipped disc saw. For each electrode, an active device chip, such as an FET based upon a silicon substrate, may be attached to the wafer surface. This attachment may be made by use of a suitable adhesive.

Leads are then attached to interconnect the active device chip with the exposed portion of the conducting layer and output leads are attached to allow interconnection of the active device chip with an indicating meter. In the case where an active device chip is not used, an output lead is connected to the exposed portion of the conducting layer to allow connection to an indicating meter.

In the final step of the process, a seal is formed on each electrode using an epoxy-filled glass sleeve, or a beeswax-filled heat-shrinkable tube, as previously discussed.

As this time, the individual ion-sensitive electrodes are ready for use. Before they will exhibit an ion-sensitive response, however, they typically must be immersed in an aqueous solution for a period of time sufficient to form a hydrated surface layer on the membrane layer, a period of time that typically takes anywhere from a few hours to a few days.

FIRST PROCESS FOR pH ELECTRODE INCLUDING THIN-FILM FORMATION OF CONDUCTING LAYER

The following portion of the specification will deal with the fabrication of a single pH electrode using a thin-film process for formation of the conducting layer.

With reference now to FIG. 5, the desired material for the substrate 20 is cut into wafers, cleaned and polished. For the application of thin-film and thick-film layers, it is well-known that substrates must have the following characteristics: (1) smoothness; (2) high strength in thin members; (3) good thermal conductivity; (4) thermal and chemical stability; (5) chemical durability; (6) high electrical resistance and low dielectric loss; (7) availability in a range of shapes and sizes; and (8) inexpensiveness.

A commonly used substrate material having the above-listed characteristics and generally well-suited for thin-film and thick-film processes is alumina (Al$_2$O$_3$). As previously noted, another requirement for the substrate material is that it be compatible with the material of the membrane layer 24. In the fabrication of the pH electrode, Corning Code 0150 glass is a desirable material for the membrane layer 24. Alumina does not have a thermal coefficient of expansion which is compatible with that of Corning Code 0150 glass and therefore is unsuitable for use as the substrate 20 inasmuch as the substrate must be heated to a fairly high temperature and then cooled with the glass in paste form thereon to form the membrane layer 24.

A ceramic material having the above-listed characteristics and having a thermal coefficient of expansion compatible with Corning Code 0150 glass is forsterite, as previously discussed. A preferable type of forsterite is that sold commercially under the trademark "ALSiMAG 243" by the Technical Ceramic Products Division of 3M Corporation.

A wafer approximately 0.5 mm. thick, as an example, is cut from a block of ALSiMAG 243 using a diamond-tipped disc saw. After cutting, the wafer is cleaned ultrasonically in both acetone and in deionized water, and dried by the use of nitrogen.

Because of the thin-film conducting layer 22 that is to be formed onto the substrate 20, it is necessary to have the substantially planar wafer surface, on which the conducting layer 22 is to be formed, to be as smooth as possible to avoid rupture of the overlying conducting layer 22. Therefore, in most cases, it is desirable to polish this wafer surface. As an example, the desired wafer surface is polished by hand for approximately 2½ hours using 400 grit silicon carbide on silk, and then for approximately 1¼ hours with one micron grit alumina on silk.

In the next step of the process, a conducting layer is formed on at least the substantially planar surface of the wafer by vapor depositing, for example, chromium, nickel and gold in successive overlying layers. The wafer is placed in a vacuum chamber (maintained at 5 × 10$^{-6}$ torr) which also includes crucibles containing the metals desired to be evaporated. The crucibles are heated sequentially to the temperatures required for metal vaporization, whereupon the metals deposit uniformly upon the substantially planar surface of the wafer. As an example, the chromium is deposited to a thickness of 656 Å ± 20%, the nickel to a thickness of 268 Å ± 20%, and the gold to a thickness of 3708 Å ± 20%. The use of chromium is desirable to form a strong bond between the conducting layer and the wafer (inasmuch as chromium forms an oxide which is compatible with the oxide of the substrate material). Nickel is used to form a layer to which solder connections could easily be made. Gold is used because of its excellent electrical conductivity, its chemical inertness and because it is not absorbed by Corning Code 0150 glass at high temperatures.

The conducting layer formed in the foregoing manner is then photoetched to achieve the desired configuration of the conducting layer 22 having the conducting strip 22a and the pads 22d, 22I e. As an example, a photograhic mask is prepared having a set of apertures therethrough corresponding to that of the desired conducting layer configuration. The wafer is then covered with a photoresist material (such as Shipley AZ 1350) and baked at 60° to 80° C. in a slight vacuum for approximately 30 minutes. The photographic mask is then placed into contact with the desired surface of the wafer and the photoresist material is exposed for approximately 30 second. Thereafter, the wafer is dipped into a developer (such as Shipley MF-312) to remove the unexposed photoresist material, and baked at 120° C. for approximately 30 minutes to harden the remaining photoresist material. An etching solution is then applied to the wafer to remove that portion of the conducting layer not covered by hardened photoresist material and acetone is used to remove the hardened photoresist material, leaving the desired conducting layer 22 on the wafer surface.

Because glass does not readily "wet" gold and therefore rolls off a gold surface when applied in a paste form and heated, it has been found desirable to form an additional conducting layer of silver on top of the gold layer in order to achieve a good glass-metal bond. As an example, approximately 1400–2000 Å of silver may be formed by electroplating. Alternatively, silver of high enough purity can be deposited to the same thickness on top of the gold by the vapor deposition process previously described before the aforementioned photoetching step.

Before the fabrication of the pH electrode can proceed, glass paste must have been prepared by reducing the pH-sensitive glass to a fine powder and mixing the powder with an appropriate organic vehicle to form a thick paste. As an example, Corning Code 0150 glass is obtained in bulk form comprising chunks each approximately ½ inch in diameter. The chunks are then broken down, using a mortar and pestle, to nuggets of a smaller size, typically ¼ inch in diameter. The nuggets are mixed with an appropriate lubricant, such as water, and the resultant mixture is placed in a conventional ball mill which is operated for a period of time sufficient to reduce the glass to particles having an average particle size of approximately one micron. The mixture is removed from the ball mill and allowed to dry, such as by drawing the mixture through filter paper and drying the residue under an infrared lamp. It may be necessary to mix the particles with acetone and to draw this mixture through filter paper to prevent the glass particles from caking during drying.

The residue, or glass powder, is then made into a glass paste by mixing the powder with an appropriate organic vehicle. A number of organic vehicle formulations may be used, such as a mixture of an organic solvent such as butyl Cellusolve acetate and an organic binder such as ethoxyl, or a mixture of carbitol acetate and cellulose, or a mixture of $\beta$-terpinol and ethyl cellulose. As an example, the glass powder may constitute anywhere from 60 to 75 weight-percent of the glass paste. To obtain a desired viscosity of the paste, small amounts of pine oil may be added.

In the next step of the process, the glass paste is applied to the wafer so that the paste overlies the desired portion of the conducting layer 22 (specifically, the conducting strip 22a and its enlarged end 22b) and contiguous portions of the surface of the substrate 20. Glass paste may be applied to the wafer by use of a wooden spatula, and is preferably applied to a nominal thickness of about one mil.

The wafer must then be heated to a first temperature to dry the paste by driving off the organic solvent and to a second, higher temperature to drive off the organic binder and to fuse the glass into the continuous membrane layer 24 and to bond the glass to the underlying conducting layer 22 and substrate 20. As an example, the wafer is placed into a furnace whose temperature is raised to approximately 100° C. for approximately ten minutes to drive off the organic solvent. The temperature of the furnace is then raised to approximately 1000° C. for about eight minutes to fuse and bond the glass. The exact value of this second temperature and the time at which the wafer is maintained at the second temperature are not critical, but are determined by the minimum temperature and time needed to lower the viscosity of the glass to a point where it will fuse into a bubble-free, thin layer. Preferably, the second temperature is the working point (viscosity = 10,000 poises) of the glass. As an example, the working point of Corning Code 0150 glass is approximately 900° C. Temperatures substantially lower than the working point will require an inordinate amount of time for membrane layer fusion. Temperatures higher than the working point, while requiring less time for membrane layer fusion, must be not so high as to lower the viscosity of the glass to a point where the glass loses its ability to retain the desired configuration or as to result in excessive sodium being lost from the glass or displaced by metal diffusion from the underlying conducting layer 22. For the pH electrode using Corning Code 0150 glass, a maximum value for the second temperature is believed to be approximately 1050° C.

The furnace is then turned off and allowed to cool. When the wafer has reached room temperature, it is removed for the next step of the process which involves the bonding of the active device chip 26 to the wafer surface. In the case where the active device chip 26 comprises a FET having a silicon substrate, the substrate may be bonded directly to the wafer surface using an appropriate epoxy resin. Alternatively, if the chip substrate is provided with a gold layer, then the chip may be bonded to the wafer surface by placing the gold layer into contact with a corresponding gold layer on the wafer surface and heating the assembly to approximately 500° C. to achieve formation of a gold-silicon eutectic bond between the silicon chip substrate, the gold layer on the chip substrate, and the corresponding gold layer on the wafer surface.

In the next step of the process, the leads 27, preferably comprising thin gold wires approximately one mil in thickness, are then ultrasonically bonded to terminals on the active device chip 26, and to the end 22c of strip 22a and to the pads 22d, 22e. The output leads 29, each preferably comprising thin, insulated, stranded copper wire, approximately 10 mils in thickness, are then soldered to the pads 22d, 22e.

To form the seal 28, a length of glass tubing is chosen having a diameter slightly bigger than the width of the substrate 20. The glass tubing is heated and one end thereof is flattened. After the glass tubing cools, the wafer is inserted into a cavity defined by the flattened end of the glass tubing so that the glass tubing surrounds that portion of the substrate 20 having the pads 22d, 22e, the active device chip 26, the output leads 29, the leads 27, the end 22c of the strip 22a, and a small portion of the strip 24a of the membrane layer 24. A potting material such as epoxy resin is introduced into the cavity formed between the glass tubing and the wafer and allowed to cure.

Figure 8:
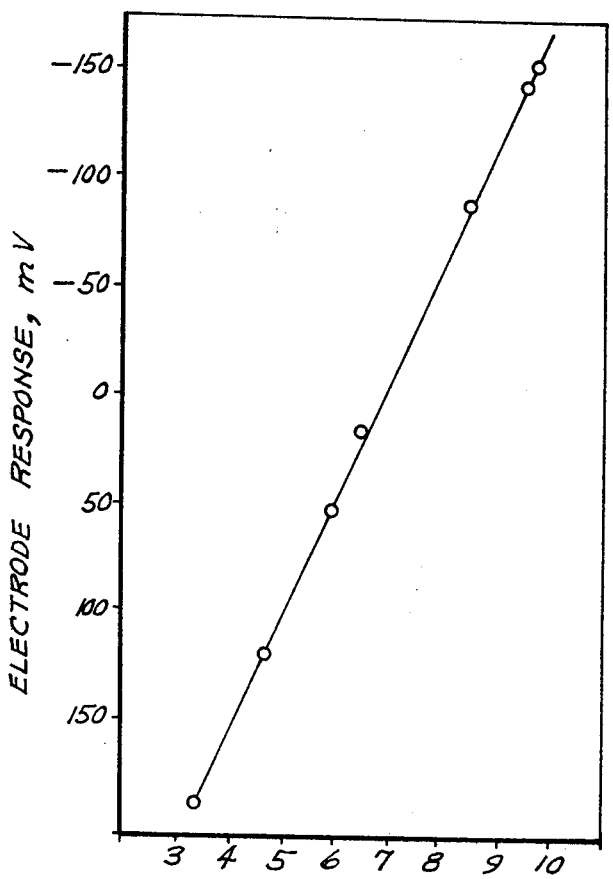
FIG. 8 is a graph illustrating the tested response of a pH electrode fabricated substantially by the first process of the present invention.

The electrode fabrication is now complete. After the electrode has been soaked in an appropriate aqueous solution for a sufficient period of time to form a hydrated layer on the surface of the membrane layer 24, the electrode is capable of providing a pH response. FIG. 8 shows the results of a test carried out using a pH electrode fabricated substantially according to the process just described (excepting that an active device chip 26 was not attached and that a single output lead 29 was connected directly to the end 22c of the strip 22a). The pH electrode and a reference electrode (of calomel) were immersed in a test solution, at a temperature of approximately 22° C., and the pH of the test solution was incrementally varied over a range of approximately 3 pH units to approximately 10 pH units. As can be seen, the potential difference between the pH electrode and the reference electrode varied linearly over the measured range at a rate of approximately 58 millivolts per pH unit, which response corresponds very well with that exhibited by prior art pH electrodes.

SECOND PROCESS FOR pH ELECTRODES INCLUDING THICK-FILM FORMATION OF CONDUCTING LAYER

The process just described for fabricating pH electrodes does not in many cases lend itself to mass-production techniques, due to the time required for the vapor deposition of the conducting layer 22 and the time required for the manual appliction of the glass paste to the wafer. The process to be described is more readily applicable to mass-production, inasmuch as the conducting layer 22 and the membrane layer 24 are each formed by thick-film screening techniques.

Figure 6:
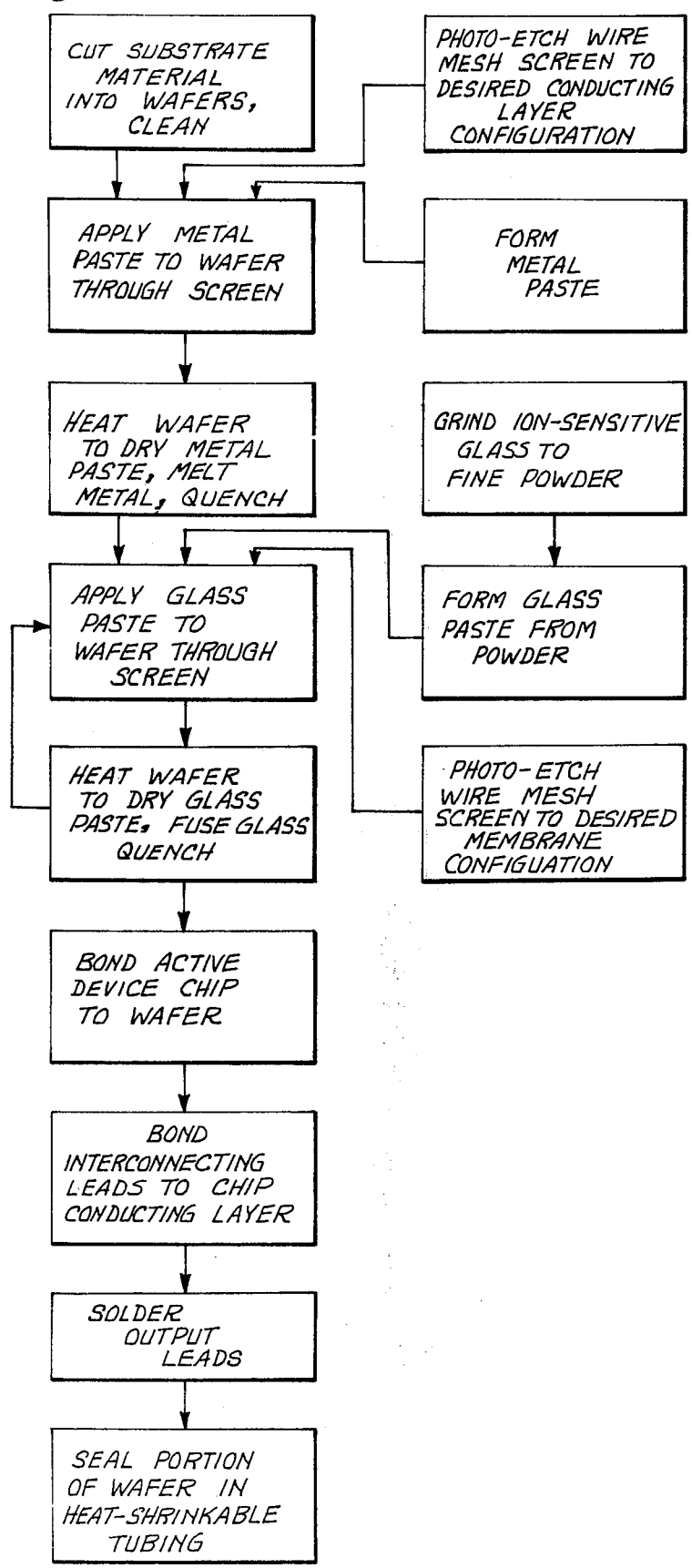
FIG. 6 is a flow chart illustrating the specific process steps of a second process of the present invention and utilizing thick-film integrated circuit techniques.

With reference now to FIG. 6, the desired substrate material, such as ALSiMAG 243, is cut into wafers of the desired thickness and cleaned as previously described. Because thick-film screening techniques are to be used, it is not essential that the wafer surface to which the glass layer 22 and the membrane layer 24 are to be applied be absolutely smooth, and therefore the polishing step of the previous process may be dispensed with.

A flat wire mesh screen is then photoetched to obtain an open region thereon having the configuration of the desired conducting layer 22. As an example, a photographic mask is produced which has a set of apertures therethrough corresponding in configuration and location to that of the strip 22a and the pads 22d and 22e. The flat wire mesh screen, at least 200 mesh and preferably 325 mesh (325 wires per inch) with a wire thickness of approximately one mil, is coated with a photoresist material, and the screen is baked to harden the photoresist material.

The photographic mask is then placed into contact with the wire mesh screen and the photoresist material is exposed. Thereafter, the exposed photoresist material is removed by dipping the wire mesh screen into an appropriate developer. As a result, the completed wire mesh screen is coated with photoresist except in the region of the desired conducting layer 22.

A paste is formed from the desired materials of the conducting layer 22. As an example, a typical paste is that available from Plessey EMD and Mix C6310 which comprises a mixture of platinum and gold in fine particle form, a small quantity of palladium in fine particle form, a small quantity of glass articles, an organic vehicle including an organic binder and an organic solvent, and other oxides. This paste includes 11 weight-percent of platinum, 60 weight-percent of gold, and 3 weight-percent of palladium, with the glass particles and the other oxides assisting in bonding of the paste when heated to the underlying wafer surface.

Figure 7:
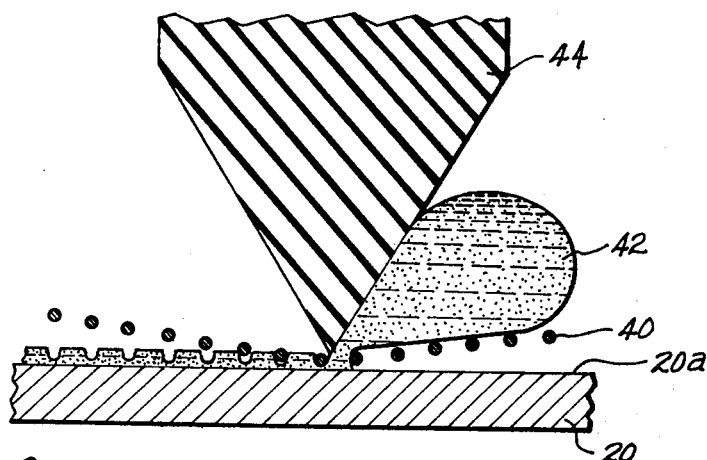
FIG. 7 is a schematic representation of a thick-film apparatus used in the second process of the present invention.

With reference now to FIG. 7, the completed wire mesh screen 40 is brought into contact with the surface 20a of the substrate 20 on which the conducting layer 22 is to be formed, and the paste 42 is applied to the screen 40 so that the paste 42 overlies at least the open region in the screen 40. A squeegee 44 is then drawn over the screen 40 to force the paste 42 through the open region in the screen and into contact with the surface 20a. When the screen 40 is removed, the paste 42 will remain on the surface 20a in the configuration of the desired conducting layer and with a thickness approximately equal to that of the screen 40 (approximately two mils).

The paste is then dried to drive off the organic solvent by heating the wafer, for example, under an infrared lamp for approximately fifteen minutes. The organic binder is then driven off and the remaining materials of the paste are fused into a continuous conducting layer bonded to the wafer surface by, for example, placing the wafer into a furnace, maintaining the furnace at a temperature of approximately 500° C. for forty-five minutes, and then raising the temperature of the furnace of 950° C. and maintaining that temperature for approximately ten minutes. The exact temperatures and times of heating are not critical and are determined by the exact metals being used for the conducting layer and by the desired physical properties of the resultant conducting layer 22, including solderability, adhesion, and resistance of the conducting layer to metal leaching upon soldering. After this step, the wafer is then cooled to room temperature by removing the wafer from the furnace. After cooling, the conducting layer 22 has the desired configuration and a thickness of approximately one-half to one mil.

In the next step of the process, a glass paste is formed using Corning Code 0150 glass in the manner previously described. As an alternative, alcohol may be used as the lubricant during the ball-milling step to avoid the sodium leaching that occurs when water is used as the lubricant, and the mixture when removed from the ball-mill may be allowed to dry by alcohol evaporation.

A second wire mesh screen is then photoetched to obtain an open region therein having the configuration of the desired membrane layer 24, in a manner similar to that used for completion of the first wire mesh screen used for the conducting layer. As a result, the completed second wire mesh screen is covered with photoresist but has an open region corresponding in configuration to that of the desired membrane layer 24.

The completed second wire mesh screen is then placed into contact with the wafer surface so that the open region in the screen is in registry with the conducting layer 22. The glass paste is applied to the completed second wire mesh screen so as to overlie at least the open region, and a squeegee is drawn over the screen to force the glass paste through the open region in the screen and into contact with the conducting layer 22 and contiguous portions of the wafer surface. When the completed second wire mesh screen is removed, the glass paste will remain on the wafer in the desired configuration of the membrane layer 24 and with a thickness approximately equal to that of the second screen (approximately two mils).

By way of example, the wafer is then placed under an infrared lamp for a period of fifteen minutes to drive off the organic solvent. The wafer is placed in a furnace which has been previously heated to a temperature of approximately 500° C. and maintained in the furnace at that temperture for approximately one hour to drive off the organic binder. Thereafter, the temperature of the furnace is raised to approximately 850° C. As soon as the temperature reaches 850° C., the wafer is quenched by removing it from the furnace and placing it on a block of aluminum.

It has been found in practice that the membrane layer 24 formed by the aformentioned thick-film screening process does not in many cases completely cover the desired portion of the conducting layer 22. Oftentimes, pinholes are exhibited in the membrane layer 24 which, if not covered, would provide a short across the membrane layer 24 when the electrode is immersed in a test solution. Accordingly, it may be necessary to repeat the aforementioned steps of thick-film screening the glass paste onto the wafer, and the steps of drying and fusing the glass paste with the application of heat until an acceptable pin-hole free, membrane layer 24 is obtained.

Thereafter, the active device chip 26 is bonded to the wafer surface, the interconnecting leads 27 are ultrasonically bonded to terminals on the active device chip 26 and to the end 22c of the strip 22a, and to the conducting pads 22d, 22e, and the output leads 29 are soldered to the conducting pads 22d, 22e in the manner previously described.

To complete the pH electrode, a length of heat-shrinkable tubing having a diameter larger than the width of the wafer is chosen and the end of the tubing is filled with an appropriate hydrophobic potting material such as beeswax. A cavity is formed in the beeswax and the wafer is inserted into the cavity so that the tubing surrounds the end of the wafer having the active device chip 26, the pads 22d, 22e, the end 22c of strip 22a, and a portion of the membrane layer 24. The wafer is then heated to a temperature sufficient to melt the beeswax and to cause the heat-shrinkable tubing to conform itself to the wafer to form the seal 28.

Figure 9:
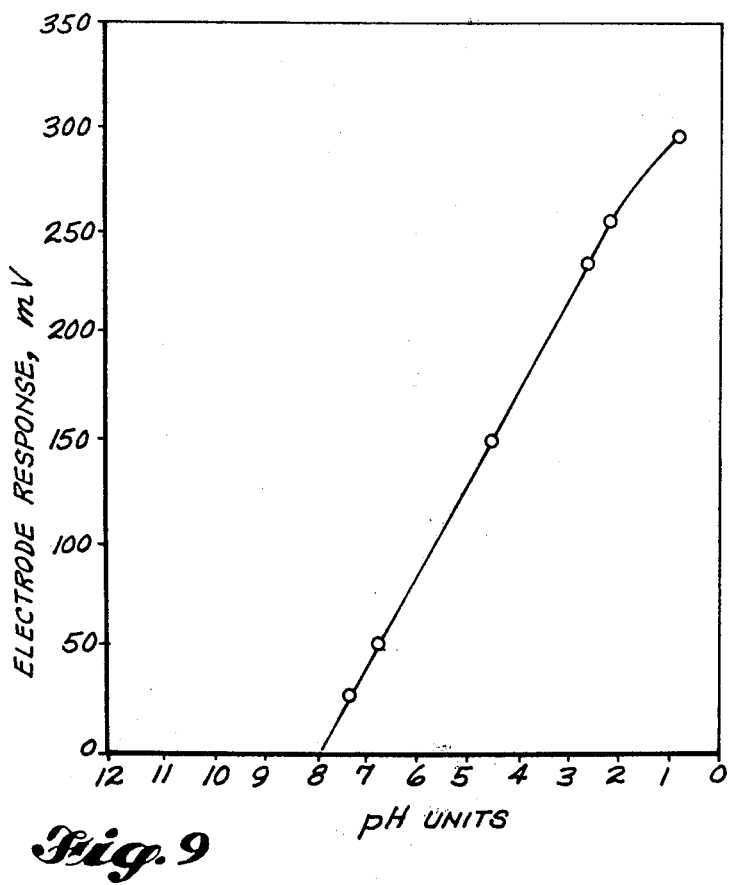
FIG. 9 is a graph illustrating the tested response of a pH electrode fabricated substantially by the second process of the present invention.

After immersion of the pH electrode in an appropriate aqueous solution for a period of time sufficient to form a hydrated surface layer, the electrode is capable of providing a pH response. FIG. 9 shows the results of a test carried out using a pH electrode fabricated substantially according to the second process (excepting that an active device chip 26 was not attached and that a single output lead 29 was soldered directly to the end 22c of strip 22a). The pH electrode and a reference electrode (of calomel) were immersed in a test solution, at a temperature of approximately 22° C., and the pH of the test solution was incrementally varied over a range of approximately 1 pH to approximately 8 pH. As can be seen, the potential difference between the pH electrode and the reference electrode varied linearly over the measured range at a rate of approximately 44 millivolts per pH unit.

OTHER ION-SENSITIVE ELECTRODES AND EQUIVALENT STRUCTURES AND PROCESSES

The structure and processes described are readily applicable to ion-sensitive electrodes other than pH-sensitive electrodes. As a first example, the processes readily permit the formation of ion-sensitive membrane layers of glasses, other than pH-sensitive glasses, which are known to the prior art as being primarily sensitive to ions other than hydrogen. Typically, each of these glasses include a specific weight percent of aluminum ($Al_2O_3$) or boron oxide ($B_2O_3$) and specific weight-percentages of silicon dioxide ($SiO_2$) and another oxide such as sodium oxide ($Na_2O$). As previously described, the choice of material for the substrate 20 must be made so that the substrate material is compatible with the physical properties of the chosen ion-sensitive glass.

It also is not necessary that the surface of the substrate, upon which the conducting and membrane layers are formed, be substantially planar, inasmuch as the thin-film vapor deposition and thick-film screening processes described, or other processes, can be adapted with the use of ordinary skill for nonplanar substrate surfaces.

As another example, an ion-sensitive electrode may be fabricated by forming a substrate material into wafers and by applying a thin conducting layer to the wafer surface by either of the thin-film vapor deposition, or thick-film screening processes described. The membrane layer 24 can then be formed by using a polymer such as polyvinyl chloride which is loaded with a certain percentage of a well-known ion-exchanging material, such as valinomycin or calcium didecylphosphate respectively sensitive to potassium ($K^+$) and calcium ($Ca^{2+}$) ions. As a specific example, an ion-sensitive electrode particularly sensitive to calcium ions (hereinafter a calcium electrode) may be fabricated by forming a ceramic substrate material, preferably alumina, into wafers, each wafer including at least one substantially planar wafer surface. The wafer is then cleaned and a thin conducting layer is formed on the substantially planar wafer surface by using a platinum-gold paste in thick-film screening process previously described. Preferably, the surface area of the conducting layer formed in this manner is made as large as possible within the confines of the substantially planar wafer surface to maximize the calcium response of the electrode. The conducting layer may be considered as having first and second regions. As previously described, an output lead may be connected to the second region of the conducting layer, or, an active device chip may be bonded to the wafer, preferably to the substantially planar wafer surface and adjacent the second region of the conducting layer, with the active device chip being interconnected with the second region of the conducting layer and with an output lead or leads. Then, a fluid-tight seal is bonded to the wafer, the conducting layer and to any output device, such as the output lead, and additionally to the active device chip and any interconnecting leads if used. The fluid-tight seal covers at least the second region of the conducting layer, and portions of the wafer and the output device adjacent the second region of the conductor. As previously described, this fluid-tight seal may be formed by using a length of beeswax-filled, heat shrinkable tubing such as that composed of polyvinyl chloride.

A calcium-sensitive membrane is then bonded to the wafer and to at least a portion of the conducting layer, the membrane including a continuous membrane layer covering the first region of the conductor and portions of the substantially planar wafer surface contiguous to the first region of the conductor. Preferably, the entire wafer is dipped into a solution containing polyvinyl chloride, a solvent such as tetrahydrafuran, and a certain percentage of calcium didecylphosphate, typically one part in six by volume. The wafer is then removed from the solution and the solvent is allowed to evaporate so that the polyvinyl chloride forms the desired membrane including the membrane layer 24. The viscosity of the solution should be controlled so that the polyvinyl chloride is capable of remaining on the wafer with a predetermined thickness, typically 50–100 microns, after the wafer is removed from the solution and the solvent is allowed to evaporate.

In this case, the choice of materials for the substrate 20 and the conducting layer 22 is not as critical as the choice of those materials in the case where the membrane layer 24 is formed from an ion-sensitive glass inasmuch as the membrane layer 24 may be formed without the application of heat.

It may be desirable in the case of the calcium electrode to form a layer of an inner reference material intermediate the conducting layer and the calcium-sensitive membrane. As an example, equal parts of mercury (Hg) and mercury chloride ($Hg_2Cl_2$) are ground together, using a mortar and pestle, to obtain a paste. A saturated potassium chloride (KCl) solution is then applied to the paste to moisten it, and the thus-moistened paste is mixed with a sufficient amount of calcium sulfate dihydrate ($CaSO_4 \cdot 2H_2O$) to saturate the paste.

The resultant inner reference paste is applied to the wafer so as to cover at least the first region of the conducting layer, and the calcium-sensitive membrane is then formed as previously described.

As yet another example, the processes are adaptable broadly to the formation of ion-sensitive membrane layers from a mixture including finely-divided precipitates, such as barium sulfate or the silver halides, and a binder or matrix material. The material for the membrane layer also may comprise a monocrystalline or polycrystalline material, such as lanthanum fluoride or the silver halides, which are sensitive to specific ions when fabricated in membrane form.

The only other requirement for the choice of material of the membrane layer 24 is that the material be capable of being formed in a continuous layer overlying a conducting layer which itself is formed on a substantially planar substrate surface.

The structure for an ion-sensitive electrode shown in FIGS. 2 and 3 can be made sensitive to a number of different ions. For example, a number of conducting layers can be formed on the substrate surface, by either of the thin-film or thick-film processes described, and overlaid with a corresponding number of membrane layers, each membrane layer being composed of a different ion-sensitive material.

In addition, since silver can be easily formed in a conducting layer on a ceramic substrate by the use of thick-film screening processes, silver-silver chloride reference electrodes can be fabricated on the same substrate on which is formed the ion-sensitive electrode.

Although a field effect transistor has been discussed as the basis of the active device chip 26, it should be apparent that other integrated circuit chips can be bonded to the substrate for the purpose of converting the high impedance of the membrane layer 24 into a low impedance output, or for other purposes. For example, the active device chip 26 may comprise a voltage-controlled oscillator integrated circuit chip functioning to convert the high impedance, DC output of the membrane layer to a low-impedance AC signal which is particularly compatible with AC-coupled, direct-reading indicating meters.

As a final example, the process steps described may be varied to suit the specific ion-sensitive electrode that is to be fabricated. It may be desirable in some instances to form the conducting layer by thin-film, vapor deposition techniques, and to form the membrane layer by thick-film screening techniques, or by other techniques apparent to those of ordinary skill in the art.

While the invention has therefore been described with respect to a preferred embodiment, it is to be clearly understood by those skilled in the art that the invention is not limited thereto, but rather that the limits of the invention are to be interpreted only in conjunction with the appended claims.

The embodiments of the invention in which an exclusive property or privilege is claimed are as follows:

1. An improved ion-sensitive electrode comprising:
   (a) a substrate formed into a wafer having a substantially planar wafer surface;
   (b) a conductor bonded to said wafer, said conductor having first and second regions, with at least said first region being formed as a conducting layer on said substantially planar wafer surface;
   (c) an ion-sensitive membrane bonded to said wafer and to at least a portion of said conductor, said membrane including a continuous membrane layer covering said first region of said conductor and portions of said substantially planar wafer surface contiguous to said first region of said conductor;
   (d) output means connected to said second region of said conductor for interconnecting said electrode with a utilization device; and
   (e) fluid-tight sealing means bonded to said wafer, to said conductor, and to said output means, said fluid-tight sealing means covering at least said second region of said conductor and portions of said wafer and said output means adjacent said second region of said conductor.

2. An electrode as recited in claim 1, wherein said ion-sensitive membrane is formed from a glass paste including an ion-sensitive glass substantially by a thick-film screening process, and wherein said substrate is a ceramic material having a coefficient of thermal expansion which is compatible with that of said ion-sensitive glass.

3. An electrode as recited in claim 2, wherein said ion-sensitive glass is a pH-sensitive glass.

4. An electrode as recited in claim 3, wherein said conductor includes a plurality of metallic layers which are formed in succession on said wafer by a vapor-deposition process.

5. An electrode as recited in claim 3, wherein said conducting layer is formed from a paste including at least one conducting material by a thick-film screening process.

6. An electrode as recited in claim 3, wherein said pH-sensitive glass is Corning Code 0150 glass, and wherein said substrate is forsterite.

7. An electrode as recited in claim 6, wherein said conductor includes a plurality of metallic layers which are formed in succession on said wafer by a vapor-deposition process.

8. An electrode as recited in claim 7, wherein said plurality of metallic layers are composed, in succession, of chromium, nickel, gold and silver.

9. An electrode as recited in claim 6, wherein said conducting layer is formed from a metal paste including a mixture of a plurality of metals by a thick-film screening process.

10. An electrode as recited in claim 9, wherein said plurality of metals include platinum and gold.

11. An electrode as recited in claim 1, wherein said conductor comprises a plurality of metallic layers formed in succession on said wafer by a vapor-deposition process.

12. An electrode as recited in claim 1, wherein said conducting layer is formed from a paste including at least one conducting material by a thick-film screening process.

13. An electrode as recited in claim 1, wherein said first and said second regions of said conductor are both formed as a continuous conducting layer on said substantially planar wafer surface.

14. An electrode as recited in claim 13, wherein said continuous conducting layer has a configuration of a first elongated strip having first and second ends which are enlarged with respect to said first elongated strip, with said first end and a portion of said elongated strip adjacent thereto comprising said first region of said conductor, and with said second end and the remaining portion of said elongated strip comprising said second region of said conductor.

15. An electrode as recited in claim 14, wherein said membrane layer has a configuration of a second elongated strip having an enlarged end, said enlarged end and said second elongated strip being complementary to but slightly larger than said first end and the portion of said first elongated strip of said conducting layer comprising said first region of said conductor.

16. An electrode as recited in claim 15, wherein said fluid-tight sealing means is also bonded to said membrane layer and covers in addition a portion of said membrane layer adjacent said second region of said conductor.

17. An electrode as recited in claim 14, wherein said continuous conducting layer further has the configuration of at least one conducting pad formed on said substantially planar wafer surface, said conducting pad being isolated from said elongated strip and adjacent said second end thereof; and, wherein said output means includes an active device chip bonded to said substantially planar wafer surface adjacent said second end of said elongated strip and said conducting pad, said active device chip having an input terminal and at least one output terminal; said output means further including first interconnecting lead means connected to said second end of said elongated strip and said input terminal of said active device chip, second interconnecting lead means connected to said output terminal of said active device chip and said conducting pad, and output lead means connected to said conducting pad for interconnecting said electrode with a utilization device; and, wherein said fluid-tight sealing means is bonded to and covers said active device chip, said first and second interconnecting lead means, and a portion of said output lead means immediately adjacent said conducting pad.

18. An electrode as recited in claim 17, wherein said active device chip includes a field effect transistor.

19. An electrode as recited in claim 13, wherein said output means includes an active device chip bonded to said wafer, said active device chip having an input terminal and at least one output terminal; interconnecting lead means connected to said second region of said conductor and said input terminal of said active device chip; and, output lead means connected to said output terminal of said active device chip for interconnecting said electrode with a utilization device; and, wherein said fluid-tight sealing means is also bonded to and covers said active device chip, said interconnecting lead means, and a portion of said output lead means immediately adjacent said output terminal on said active device chip.

20. An electrode as recited in claim 19, wherein said active device chip includes a field effect transistor.

21. An electrode as recited in claim 19, wherein said active device chip is bonded to said substantially planar wafer surface adjacent said second region of said conductor.

22. An electrode as recited in claim 13, wherein said output means includes an output lead connected to said second region of said conductor for interconnecting said electrode with a utilization device; and, wherein said fluid-tight sealing means is bonded to and covers a portion of said output lead immediately adjacent said second region of said conductor.

23. An electrode as recited in claim 1, wherein said output means includes an active device chip bonded to said wafer, said active device chip having an input terminal and at least one output terminal; interconnecting lead means connected to said second region of said conductor and said input terminal of said active device chip; and, output lead means connected to said output terminal of said active device chip for interconnecting said electrode with a utilization device; and, wherein said fluid-tight sealing means is also bonded to and covers said active device chip, said interconnecting means, and a portion of said output lead means immediately adjacent said output terminal of said active device chip.

24. An electrode as recited in claim 23, wherein said active device chip includes a field effect transistor.

25. An electrode as recited in claim 23, wherein said active device chip is bonded to said substantially planar wafer surface adjacent said second region of said conductor.

26. An electrode as recited in claim 1, wherein said output means includes an output lead connected to said second region of said conductor for interconnecting said electrode with a utilization device; and, wherein said fluid-tight sealing means is bonded to and covers a portion of said output lead immediately adjacent said second region of said conductor.

27. An electrode as recited in claim 1, wherein said fluid-tight sealing means comprises: a body having a cavity therein, said wafer being received in said cavity so that said body covers at least said second region of said conductor and portions of said wafer adjacent said second region; and, a potting material contained within and filling said cavity.

28. An electrode as recited in claim 27, wherein said body comprises a length of glass tubing, and said potting material comprises an epoxy resin.

29. An electrode as recited in claim 27, wherein said body comprises a length of heat-shrinkable tubing, and said potting material comprises beeswax.

30. An electrode as recited in claim 1, wherein said ion-sensitive membrane is formed from a polymer loaded with an ion-exchanging material.

31. An electrode as recited in claim 30, wherein said polymer is polyvinyl chloride.

32. An electrode as recited in claim 30, wherein said ion-exchanging material is calcium didecylphosphate.

33. An electrode as recited in claim 30, wherein said ion-exchanging material is valinomycin.

34. An electrode as recited in claim 30, wherein said electrode further comprises a layer of inner reference material interposed between said first region of said conductor and said ion-sensitive membrane.

35. A process for fabricating an ion-sensitive electrode, said process comprising the steps of:
 (a) fabricating a wafer from a substrate material, said wafer having a substantially planar wafer surface;

(b) forming a continuous conducting layer having a desired configuration on said substantially planar wafer surface;

(c) forming a continuous ion-sensitive membrane layer on a first region of said continuous conducting layer and portions of said substantially planar wafer surface contiguous to said first region of said continuous conducting layer;

(d) connecting at least one lead to a second region of said continuous conducting layer; and (e) forming a fluid-tight seal over at least said second region of said continuous conducting layer, portions of said substantially planar wafer surface contiguous to said second region, and a portion of said lead adjacent said second region.

36. A process as recited in claim 35, wherein said continuous conducting layer is formed by a thin-film, vapor deposition subprocess.

37. A process as recited in claim 36, wherein said thin-film, vapor deposition subprocess includes the substeps of:

(a) polishing and cleaning said substantially planar wafer surface;

(b) placing said wafer into an evacuated chamber along with a quantity of at least one metal, and heating said metal to a temperature sufficient to vaporize said metal so that said metal uniformly deposits in a continuous conducting layer on at least said substantially planar wafer surface;

(c) removing said wafer from said evacuated chamber; and (d) photoetching said continuous conducting layer to leave on said substantially planar wafer surface only that portion of said continuous conducting layer having the desired configuration.

38. A process as recited in claim 37, wherein said thin-film, vapor deposition subprocess includes the further substeps of placing a quantity of at least one other metal into said evacuated chamber and heating said one other metal in succession to said one metal to uniformly deposit said one other metal in a successive continuous layer upon said wafer.

39. A process as recited in claim 35, wherein said continuous conducting layer is formed by a thick-film screening subprocess.

40. A process as recited in claim 39, wherein said thick-film screening subprocess includes the substeps of:

(a) preparing a first wire mesh screen having a predetermined mesh and a thickness approximating that of the desired conducting layer, said first wire mesh screen also having an open region therethrough corresponding in configuration to that of the desired conducting layer;

(b) preparing a paste by mixing, with an organic vehicle including an organic solvent and an organic binder, a conducting material in particle form, said conducting material having an average particle size less than said predetermined mesh of said first wire mesh screen;

(c) bringing said first wire mesh screen into contact with said substantially planar wafer surface and spreading said paste on said wire mesh screen to cover at least said open region therethrough;

(d) forcing said paste through said open region in said first wire mesh screen and into contact with said substantially planar wafer surface; and, (e) removing said first wire mesh screen and heating said wafer to a first temperature for a time sufficient to drive off said organic solvent and then to at least a second temperature for a time sufficient to drive off said organic binder and to fuse said conducting material into a continuous conducting layer; and, (f) allowing said wafer to cool.

41. A process as recited in claim 40, wherein said conducting material includes at least one metal.

42. A process as recited in claim 35, wherein said ion-sensitive membrane layer is formed by a thick-film screening subprocess.

43. A process as recited in claim 42, wherein said thick-film screening subprocess includes the substeps of:

(a) preparing a second wire mesh screen having a predetermined mesh and a thickness approximating that of the desired ion-sensitive membrane layer, said second wire mesh screen having an open region therethrough corresponding in configuration to that of the desired ion-sensitive membrane layer;

(b) preparing a membrane paste by mixing, with an organic vehicle including an organic solvent and an organic binder, a paste material including an ion-sensitive membrane material in particle form, said ion-sensitive membrane material having an average particle size less than said predetermined mesh of said second wire mesh screen;

(c) bringing said second wire mesh screen into contact with said substantially planar wafer surface so that said open region therein is in registration with said continuous conducting layer, and spreading said membrane paste on said second wire mesh screen to cover at least said open region therethrough;

(d) forcing said membrane paste through said open region in said second wire mesh screen and into contact with said conducting layer and contiguous portions of said substantially planar wafer surface;

(e) removing said second wire mesh screen and heating said wafer to a first temperature for a time sufficient to drive off said organic solvent, and then to at least a second temperature for a time sufficient to drive off said organic binder and to fuse said membrane material into a continuous ion-sensitive membrane layer; and (f) quickly quenching said wafer to substantially room temperature.

44. A process as recited in claim 43, wherein said substeps (c), (d), (e) and (f) are repeated until a continuous, pin-hole free, ion-sensitive membrane layer is formed.

45. A process as recited in claim 43, wherein said ion-sensitive material is an ion-sensitive glass.

46. A process as recited in claim 45, wherein said second temperature is approximately the working point of said ion-sensitive glass.

47. A process as recited in claim 35, further comprising the steps of:

(a) bonding an active device chip to said substantially planar wafer surface, said active device chip including an input terminal and at least one output terminal;

(b) bonding a first lead to said second region of said conducting layer and to said input terminal of said active device chip;

(c) connecting a second lead to said output terminal of said active device chip; and, (d) forming said fluid-tight seal additionally over said first lead, said active device chip, and a portion of said second lead adjacent said active device chip.

48. A process as recited in claim 47, further comprising the steps of:
    (a) forming said continuous conducting layer into a configuration also including a pad isolated from said second region thereof on said substantially planar wafer surface;
    (b) bonding a third lead to said output terminal of said active device chip and to said pad;
    (c) connecting said second lead to said pad; and
    (d) forming said fluid-tight seal additionally over said third lead and said pad.

49. A process as recited in claim 35, wherein said step of forming said fluid-tight seal includes the substeps of:
    (a) flattening one end of a length of tubing to define a cavity therein complementary in configuration to said wafer;
    (b) passing said at least one lead through said length of tubing and out the other end thereof and inserting said wafer into said cavity so that said flattened end overlies at least all of said second region of said continuous conducting layer; and
    (c) completely filling said cavity with a potting material.

50. A process as recited in claim 49, wherein said tubing is composed of glass.

51. A process as recited in claim 49, wherein said potting material is an epoxy resin.

52. A process as recited in claim 35, wherein said step of forming said fluid-tight seal includes the substeps of:
    (a) filling one end of a length of heat-shrinkable tubing with a potting material and forming a cavity in said potting material which is complementary in configuration to said wafer;
    (b) passing said at least one lead through said length of heat-shrinkable tubing and out the other end thereof, and inserting said wafer into said cavity so that said length of heat-shrinkable tubing overlies at least all of said second region of said continuous conducting layer; and
    (c) heating said wafer so that said heat-shrinkable tubing conforms to said wafer.

53. A process as recited in claim 52, wherein said heat-shrinkable tubing is composed of polyvinyl chloride.

54. A process as recited in claim 52, wherein said potting material is composed of beeswax.

55. A process for fabricating a pH electrode, said process comprising the steps of:
    (a) fabricating a wafer from a ceramic substrate material, said wafer having a substantially planar wafer surface;
    (b) forming a continuous conducing layer having a desired configuration on said substantially planar wafer surface;
    (c) forming a continuous membrane layer from a pH-sensitive glass on a first region of said continuous conducting layer and portions of said substantially planar wafer surface contiguous to said first region, said ceramic substrate material having a coefficient of thermal expansion compatible with that of said pH-sensitive glass;
    (d) connecting at least one lead to a second region of said continuous conducting layer; and
    (e) forming a fluid-tight seal over at least said second region of said continuous conducting layer, portions of said substantially planar wafer surface contiguous to said second region, and a portion of said lead adjacent said second region.

56. A process as recited in claim 55, wherein said pH-sensitive glass has a nominal mole-percent composition of 22% $Na_2O$, 6% $CaO$, and 72% $SiO_2$, and said ceramic substrate material is forsterite.

57. A process as recited in claim 56, wherein said step of forming said continuous conducting layer is accomplished by forming in succession a plurality of thin-film layers of chromium, nickel, gold and silver in the configuration of the desired conducting layer, and wherein said lead is connected by soldering to said second region of said conducting layer.

58. A process as recited in claim 57, wherein said chromium, nickel, and gold layers have thicknesses of approximately 656 Å, 268 Å and 37 8 Å, respectively and wherein said silver layers has a thickness in the range of 1400–2000 Å.

59. A process as recited in claim 56, wherein said step of forming said continuous conducting layer is accomplished by thick-film screening of a metal paste.

60. A process as recited in claim 59, wherein said step of forming a continuous conducting layer comprises the substeps of:
    (a) preparing a metal paste consisting of gold of approximately 60 weight-percent, platinum of approximately 11 weight-percent, both said gold and said platinum being in fine particle form, said metal paste also consisting of glass particles and other oxide particles, and also consisitng of an organic vehicle including an organic binder and an organic solvent;
    (b) preparing a first wire mesh screen of at least 200 wire mesh and a thickness of approximately 2 mils, said first wire mesh screen having an open region therethrough corresponding in configuration to that of the desired conducting layer;
    (c) bringing said first wire mesh screen into contact with said substantially planar wafer surface and spreading said metal paste on said wire mesh screen to cover at least said open region therethrough;
    (d) forcing said metal paste through said open region in said first wire mesh screen and into contact with said substantially planar wafer surface;
    (e) removing said first wire mesh screen and heating said wafer under an infrared lamp for approximately 15 minutes to drive off said organic solvent, then heating said wafer to a temperature of approximately 500° C. for 45 minutes and then to a temperature of 950° C. for approximately 10 minutes to drive off said organic binder and to fuse said gold and platinum into a continuous conducting layer; and
    (f) allowing said wafer to cool.

61. A process as recited in claim 56, wherein said membrane layer is formed from a glass paste including said pH sensitive glass.

62. A process as recited in claim 61, wherein said step of forming said membrane layer comprises the substeps of:
    (a) reducing said pH sensitive glass to a fine powder having an average particle size of approximately 1 micron;
    (b) mixing said fine powder with an organic vehicle including an organic binder and an organic solvent to form a glass paste, said glass paste comprising approximately 60–75 weight-percent of said pH sensitive glass;

(c) applying said glass paste to said wafer so that said glass paste overlies said first region of said continuous conducting layer and contiguous portions of said substantially planar wafer surface;

(d) heating said wafer to a first temperature for a period of time sufficient to drive off said organic solvent;

(e) heating said wafer to at least a second, higher temperature for a period of time sufficient to drive off said organic binder and to fuse said glass into a continuous membrane layer; and (f) quickly quenching said wafer to substantially room temperature.

63. A process as recited in claim 62, wherein said first temperature is approximately 100° C. and wherein said wafer is maintained at said first temperature for approximately 10 minutes.

64. A process as recited in claim 62, wherein said second temperature is approximately 1000° C., and wherein said wafer is maintained at said second temperature for approximately 8 minutes.

65. A process as recited in claim 62, wherein said substep (c) is accomplished by preparing a second wire mesh screen of at least 200 mesh and a thickness of approximately 2 mils, said second wire mesh screen having an open region therethrough corresponding in configuration to that of the desired membrane layer; bringing said second wire mesh screen into contact with said substantially planar wafer surface so that said open region therethrough is in registration with said continuous conducting layer; and spreading said glass paste onto said second wire mesh screen to cover at least said open region therethrough; forcing said glass paste through said open region in said second wire mesh screen and into contact with said first region of said continuous conducting layer and contiguous portions of said substantially planar wafer surface; and removing said second wire mesh screen.

66. A process as recited in claim 65, wherein said first temperature is that obtained when the wafer is placed under an infrared lamp, and wherein said wafer is maintained under said infrared lamp for approximately 5 minutes.

67. A process as recited in claim 65, wherein said substep (e) is achieved by placing the wafer in a furnace, the furnace having been previously heated to a temperature of approximately 500° C., and maintaining the wafer in the furnace at approximately 500° C. for approximately 1 hour, and thereafter raising the temperature of the furnace to approximately 850° C. and removing the wafer from the furnace as soon as the temperature reaches approximately 850° C.

68. A process for fabricating an ion-sensitive electrode, said process comprising the steps of:

(a) fabricating a wafer from a ceramic substrate material, said wafer having a substantially planar wafer surface;

(b) forming a continuous conducting layer having a desired configuration on said substantially planar wafer surface, said continuous conducting layer being divided into first and second regions;

(c) connecting at least one lead to said second region of said continuous conducting layers;

(d) forming a fluid-tight seal over said second region of said continuous conducting layer, portions of said substantially planar wafer surface contiguous to said second region, and a portion of said lead adjacent said second region; and (e) forming an ion-sensitive membrane on said wafer by dipping said wafer into a solution including a polymer, an ion-exchanging material, and a solvent therefor so that said solution covers at least said first region of said continuous conducting layer, and removing said wafer from said solution and allowing said solvent to evaporate.

69. A process as recited in claim 68, wherein said membrane is sensitive to calcium ions and said ion-exchanging material is calcium didecylphosphate.

70. A process as recited in claim 69, wherein said polymer is polyvinyl chloride.

71. A process as recited in claim 68, wherein said polymer is polyvinyl chloride.

72. A process as recited in claim 68, further comprising the step of forming a layer of an inner reference material upon said first region of said continuous conducting layer before said step of forming said ion-sensitive membrane.

73. A process as recited in claim 72, wherein said step of forming a layer of an inner reference material comprises the substeps of:

(a) grinding together substantially equal parts of mercury and mercury chloride to obtain a paste;

(b) moistening said paste with a saturated solution of potassium chloride;

(c) saturating the thus-moistened paste with calcium sulfate dihydrate; and (d) applying said paste to said first region of said continuous conducting layer.

74. An improved ion-sensitive electrode comprising:

(a) a substrate having a substrate surface;

(b) a conductor bonded to said substrate, said conductor having first and second regions, with at least said first region being formed as a conducting layer on said substrate surface;

(c) an ion-sensitive membrane bonded to said substrate and to at least a portion of said conductor, said membrane including a continuous membrane layer covering said first region of said conductor and portions of said substrate surface contiguous to said first region of said conductor;

(d) output means connected to said second region of said conductor for interconnecting said electrode with a utilization device; and (e) fluid-tight sealing means bonded to said substrate, to said conductor, and to said output means, said fluid-tight sealing means covering at least said second region of said conductor and portions of said substrate and said output means adajacent said second region of said conductor.

75. An electrode as recited in claim 74, wherein said ion-sensitive membrane is formed from an ion-sensitive glass.

76. An electrode as recited in claim 75, wherein said ion-sensitive glass is a pH-sensitive glass.

77. An electrode as recited in claim 74, wherein said conductor includes a plurality of metallic layers formed in succession on said substrate.

78. An electrode as recited in claim 77, wherein said plurality of metallic layers are formed by a vapor deposition process.

79. An electrode as recited in claim 74, wherein said output means includes an active device chip bonded to said substrate, said active device chip having an input terminal and at least one output terminal; interconnecting lead means connected to said second region of said cconductor and said input terminal of said active device chip; and, output lead means connected to said output terminal of said active device chip for interconnecting said electrode with a utilization device; and, wherein said fluid-tight sealing means is also bonded to and covers said active device chip, said interconnecting means, and a portion of said output lead means immediately adjacent said output terminal of said active device chip.

80. An electrode as recited in claim 79, wherein said active device chip includes a field effect transistor.

81. An electrode as recited in claim 74, wherein said output means includes an output lead connected to said second region of said conductor for interconnecting said electrode with a utilization device; and, wherein said fluid-tight sealing means is bonded to and covers a portion of said output lead immediately adjacent said second region of said conductor.

82. An electrode as recited in claim 74, wherein said fluid-tight sealing means comprises: a body having a cavity therein, said substrate being received in said cavity so that said body covers at least said second region of said conductor and portions of said substrate adjacent said second region; and, a potting material contained within and filling said cavity.

83. An electrode as recited in claim 74, wherein said ion-sensitive membrane is formed from a polymer loaded with an ion-exchanging material.

84. An electrode as recited in claim 83, wherein said polymer is polyvinyl chloride.

85. An electrode as recited in claim 83, wherein said ion-exchanging material is calcium didecylphosphate.

86. An electrode as recited in claim 83, wherein said ion-exchanging material is valinomycin.

87. An electrode as recited in claim 83, wherein said electrode further comprises a layer of inner reference material interposed between said first region of said conductor and said ion-sensitive membrane.

88. A process for fabricating an ion-sensitive electrode, said process comprising the steps of:
(a) fabricating a substrate from a substrate material, said substrate having a substrate surface;
(b) forming a continuous conducting layer having a desired configuration on said substrate surface;
(c) forming a continuous ion-sensitive membrane layer on a first region of said continuous conducting layer and portions of said substrate surface contiguous to said first region of said continuous conducting layer;
(d) connecting at least one lead to a second region of said continuous conducting layer; and
(e) forming a fluid-tight seal over at least said second second region of said continuous conducting layer, portions of said substrate surface contiguous to said second region, and a portion of said lead adjacent said second region.

89. A process as recited in claim 88, wherein said continuous conducting layer is formed by a thin-film, vapor deposition subprocess.

90. A process as recited in claim 88, wherein said continuous conducting layer is formed by a thick-film screening subprocess.

91. A process as recited in claim 88, wherein said ion-sensitive membrane layer is formed by a thick-film screening subprocess.

92. A process as recited in claim 88, further comprising the steps of:
(a) bonding an active device chip to said substrate surface, said active device chip including an input terminal and at least one output terminal;
(b) bonding a first lead to said second region of said conducting layer and to said input terminal of said active device chip;
(c) connecting a second lead to said output terminal of said active device chip; and
(d) forming said fluid-tight seal additionally over said first lead, said active device chip, and a portion of said second lead adjacent said active device chip.

93. A process as recited in claim 88, wherein said ion-sensitive membrane layer is formed by dipping said substrate into a solution including a polymer, an ion-exchanging material, and a solvent therefor so that said solution covers at least said first region of said continuous conducting layer, and removing said substrate from said solution and allowing said solvent to evaporate.

94. A process as recited in claim 93, wherein said membrane is sensitive to calcium ions and said ion-exchanging material is calcium didecylphosphate.

95. A process as recited in claim 93, wherein said polymer is polyvinyl chloride.

96. A process as recited in claim 93, further comprising the step of forming a layer of an inner reference material upon said first region of said continuous conducting layer before said step of forming said ion-sensitive membrane layer.

* * * * *

UNITED STATES PATENT AND TRADEMARK OFFICE
CERTIFICATE OF CORRECTION

PATENT NO. : 4,133,735

DATED : January 9, 1979

INVENTOR(S) : Martin A. Afromowitz et al.

It is certified that error appears in the above-identified patent and that said Letters Patent are hereby corrected as shown below:

Column 1, line 23: "$Na^{30}$" is changed to —$Na^+$—.

Column 1, line 24: "are" is changed to —and—.

Column 1, line 50: "norminal" is changed to —nominal—.

Column 1, line 56: "exchanger" is changed to —exchange—.

Column 3, line 16: "performed" is changed to —preformed—.

Column 7, line 46: "proces" is changed to —process—.

Column 11, line 68: "A1" is changed to —Al—.

Column 12, line 60: "22I e" is changed to —22e—.

Column 13, line 1: "second" is changed to —seconds—.

Column 16, line 18: "of", second occurrence, is changed to —to—.

Column 26, line 17: "37 8" is changed to —3708—.

Column 27, line 65: "layers" is changed to —layer—.

Column 29, line 2: "cconductor" is changed to —conductor—.

Column 30, line 5: "second" is deleted.

Signed and Sealed this

Seventeenth Day of April 1979

[SEAL]

Attest:

RUTH C. MASON
*Attesting Officer*

DONALD W. BANNER
*Commissioner of Patents and Trademarks*